(12) United States Patent
Sklar et al.

(10) Patent No.: US 6,638,481 B2
(45) Date of Patent: *Oct. 28, 2003

(54) PLUG FLOW CYTOMETRY FOR HIGH THROUGHPUT SCREENING AND DRUG DISCOVERY

(75) Inventors: Larry A. Sklar, Albuquerque, NM (US); Bruce S. Edwards, Albuquerque, NM (US); Frederick W. Kuckuck, III, Alburquerque, NM (US)

(73) Assignee: Science and Technology Corporation @ UNM, Albuquerque, NM (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/955,154

(22) Filed: Sep. 19, 2001

(65) Prior Publication Data

US 2002/0015664 A1 Feb. 7, 2002

Related U.S. Application Data

(62) Division of application No. 09/330,259, filed on Jun. 10, 1999, now Pat. No. 6,315,952
(60) Provisional application No. 60/103,044, filed on Oct. 5, 1998.

(51) Int. Cl.[7] ............... B32B 5/02; G01N 21/00; G01N 33/48; G01N 1/00; F16K 1/00

(52) U.S. Cl. ............... 422/63; 422/68.1; 422/70; 422/81; 422/82; 73/863; 73/863.44; 73/863.45; 137/247; 251/286; 251/304; 251/318

(58) Field of Search ............... 422/63, 62, 100, 422/68.1, 70, 81, 82; 73/863.73, 863, 863.44, 863.45; 436/161; 251/12, 56, 61, 281, 282, 283, 286, 304, 318; 137/247

(56) References Cited

U.S. PATENT DOCUMENTS

| | | | | |
|---|---|---|---|---|
| 4,352,780 A | * | 10/1982 | Schick | 422/67 |
| 5,419,208 A | * | 5/1995 | Schick | 73/863.73 |
| 5,468,643 A | * | 11/1995 | Su et al. | 436/161 |
| 5,558,838 A | * | 9/1996 | Uffenheimer | 422/100 |
| 5,691,486 A | * | 11/1997 | Behringer et al. | 73/863.73 |
| 5,783,450 A | * | 7/1998 | Yoshida et al. | 436/161 |
| 6,190,614 B1 | * | 2/2001 | Fukunaga | 422/100 |
| 6,315,952 B1 | * | 11/2001 | Sklar et al. | 422/63 |

* cited by examiner

Primary Examiner—Jill Warden
Assistant Examiner—Brian Sines
(74) Attorney, Agent, or Firm—Jagtiani + Guttag

(57) ABSTRACT

An apparatus for drawing and supplying multiple samples for rapid processing in flow cytometry. The apparatus comprises a reciprocating valve and at least one syringe. The invention is also a method for rapidly processing multiple samples in flow cytometry using the apparatus.

12 Claims, 4 Drawing Sheets

PLUG FLOW CYTOMETRY FOR HIGH THROUGHPUT SCREENING AND DRUG DISCOVERY

CROSS-REFERENCE TO RELATED APPLICATIONS

This application is a divisional application of U.S. application Ser. No. 09/330,259, filed Jun. 10, 1999, now U.S. Pat. No. 6,315,952, which claimed the benefit of the filing date of U.S. Provisional Patent Application Serial No. 60/103,044, entitled "Plug-Flow Cytometry for High Throughput Screening and Drug Discovery", filed on Oct. 5, 1998. The entire disclosure and contents of the above-identified utility patent application and provisional patent application are hereby incorporated by reference.

GOVERNMENT RIGHTS

The U.S. Government has a paid-up license in this invention and the right in limited circumstances to require the patent owner to license others on reasonable terms as provided for by the terms of Contract No. P20RR11830 awarded by U.S. National Institute of Health.

BACKGROUND OF THE INVENTION

1. Field of the Invention (Technical Field)

The present invention relates to an apparatus for processing multiple plug samples in an automated fashion for flow cytometry, using a plurality of sample loops, a reciprocating valve, and at least one syringe or pump. The present invention is also a method for rapidly processing multiple samples in flow cytometry.

2. Background Art

Flow cytometry is a tool frequently utilized for cellular analysis. In flow cytometry, a sample containing cells (or equivalent particles) is passed through a line with a sheath fluid, and focused through an orifice, with the objective of cells entering the detector one at a time. These individual cells are irradiated with a light beam, and the intensity of scattered light or fluorescent light from the cells is measured. The ability of flow cytometry to make quantitative measurements on microspheres or cells with continuous kinetic resolution offers an attractive platform for more detailed characterization of compounds of interest.

Traditionally, samples are injected into and suspended within a sheath flow. This type of delivery is disclosed in the following patents: U.S. Pat. No. 5,824,269, to Kosaka et al., entitled Flow Cytometer European Patent No. 46,345, to Connell, entitled Controlled Hydrodynamic Flow in Flow Cytometry Systems; U.S. Pat. No. 5,374,398, to Isami et al., entitled Apparatus for Analyzing Particles; U.S. Pat. No. 5,369,137, to Hansen, entitled Simultaneous Multiple Assays; and U.S. Pat. No. 5,286,452, to Hansen entitled Simultaneous Multiple Assays. The articles Hodder, P. et al., *Microfabricated Flow Chamber for Fluorescence-based Chemistries and Stopped-flow Injection Cytometry*, Analyst, 122:883–887 (1997); and Nolan, J. et al., *A Rapid Mix Flow Cytometer with Subsecond Kinetic Resolution*, Cytometry, 21(3):223–229 (1995), disclose the use of syringe pumps for a stopped-flow injection analysis. The sample stream is bounded by the reagent stream. A stopping of the sheath flow causes the core to expand the sheath, thus mixing the sample with the reagent. These inventions do not "compartmentalize" the sample, or prevent mixing. Lack of mixing is especially desirable when screening a multitude of samples, in order to prevent the possibility of cross-contamination.

One rapidly expanding field for which such cellular information is useful is that of drug discovery. Large combinatorial libraries that potentially alter or mimic receptor-ligand interactions are screened. To efficiently perform such tasks, rapidity and automation of sample handling are required.

Various devices have been developed to address sample handling. These include use of a packet type of sample delivery. U.S. Pat. No. 5,268,147, to Zabetakis et al., entitled Reversible Direction Capsule Chemistry Sample Liquid Analysis System and Method, discloses supply tubes for samples, reagents, buffers, and isolation liquid. The device functions with a positive displacement pump. Air is introduced at intervals to separate the samples. This does not result in a continuous, uninterrupted flow. Samples are not loaded while others are transferred, thus increasing processing time. U.S. Pat. No. 4,853,336, to Saros et al., entitled Single Channel Continuous Flow System, discloses sample segments separated by immiscible segments in a single conduit, which are then removed to combine and mix. While this is a continuous flow system, the goal of this invention is mixture of the sample prior to sampling. A major problem with introducing air bubbles or mixing, however, is the potential of the bubbles lodging in troublesome areas such as the analysis region of the flow cell. Also, air bubbles can be broken up and dispersed at connector junctions, causing inaccuracies in the sample draw.

Another method developed to increase sample delivery rate is the use of loops. Inventions containing loops include the following: U.S. Pat. No. 5,788,927, to Farrell, et al., entitled Unified Fluid Circuit Assembly for a Clinical Hematology Instrument, utilizes loops that align with the reagent passageways, but not samples. In Farrell, the shear valve is rinsed after each sample, so it does not disclose continuous sampling. U.S. Pat. No. 4,957,009, to Nohl et al., entitled Pushloop Liquid Sampling Method, discloses a six-port valve which pulls a sample past a loop, then pushes it back into the chamber. This device, as well, includes a flushing or rinsing step, and therefore is not a continuous delivery device. U.S. Pat. No. 4,224,033, to Hansen et al., entitled Programmable, Continuous Flow Analyzer, discloses utilizing valves to switch loops in order to add samples and reagents to carriers. This method involves inserting the samples within the carriers and subsequently mixing the sample with the carrier.

Yet another approach is the use of valves to increase sample processing speed. Such inventions include the following: U.S. Pat. No. 3,921,439, to Burns, entitled Method and Apparatus for Selectively Removing Immiscible Fluid Segments from a Fluid Sample Stream, discloses a series of valves within conduits. The function of these valves is to remove immiscible fluid segments prior to sampling. Therefore, they do not contribute to the sample, but rather function to take away from the sample. U.S. Pat. No. 5,776,781, to Vardanega et al., entitled Sterile Flow Cytometer and Sorter with Mechanical Isolation between Flow Chamber and Sterile Enclosure and Methods for Using Same, and U.S. Pat. No. 5,641,457, to Vardanega et al., entitled Sterile Flow Cytometer and Sorter with Mechanical Isolation between Flow Chamber and Sterile Enclosure, disclose injecting cells into a sheath fluid by the force of air pressure. The valves are used to regulate flow, and convert operating mode from back-flush to sort, etc. U.S. Pat. No. 5,395,588, to North, Jr., et al., entitled Control of Flow Cytometer Having Vacuum Fluidics, discloses a device that utilizes a pump to pull samples. It has four normally closed solenoid actuated valves, two of which open to the sample, and two of which open to drain the device. They are not reciprocating. U.S. Pat. No. 5,488,469, to Yamamoto, et al., entitled Cell Analyzing Apparatus, discloses a device that uses cell fluorescence analysis. It has a sample pump to draw the sample out of the tube, and a three-way valve which switches to allow the sheath fluid to be pumped past the sample, drawing it into the feed tube. These inventions utilize either air pressure or a pump to pull the sample, which may cause problems with sample handling such as creation of air bubbles and the need to flush the system between the samples.

Still a further approach to automate sample handling is described in U.S. Pat. No. 4,177,677, to Ruzicka et al., entitled Sample Supply to Automatic Analyzers, disclosing a valve which couples a sample conduit to a sample and, alternatively, to a carrier stream leading to an analytical device. The sample is pumped up to the sample conduit, then back through the carrier conduit to the analyzer. This device allows for samples of 30 $\mu$l or more to be processed, but is limited to processing one sample draw at a time.

Other inventions which disclose injecting the sample or another fluid, but lack the other aspects involved in the present invention (i.e. plugs and reciprocating valves), include U.S. Pat. No. 5,464,752, to Kortright, et al., entitled Automated Analyzer for Screening Cells or Formed Bodies for Enumeration of Populations Expressing Selected Characteristics; U.S. Pat. No. 5,221,521, to Hashizumi et al., entitled Sample Liquid Dilution System for Analytical Measurements; U.S. Pat. No. 5,080,866, to Petty et al., entitled Analytic Apparatus and Method; and U.S. Pat. No. 4,399,225, to Hansen et al., entitled Stop-Flow Analysis.

None of the previous inventions are capable, due to design constraints, of processing multiple samples in a fashion rapid enough to effectively screen large libraries. To address this need, the present invention is a novel approach to automated sample handling, disclosing a continuously flowing steam of fluid into which individual samples are sequentially inserted as a bolus or "plug" of precisely defined volume. The stream delivers the sample plugs, separated by empty volumes of fluid (the buffer of which the stream is composed), to the point of analysis in the laser beam. Because an automated syringe was used for sample uptake, pressurization of the sample-containing vessel was unnecessary. This system leads to faster sampling rates and smaller required sample volumes.

SUMMARY OF THE INVENTION (DISCLOSURE OF THE INVENTION)

A preferred embodiment of the present invention comprises an apparatus for transferring a plurality of samples, the apparatus comprising a plurality of sample loops for receiving a plurality of samples, at least one syringe or pump for moving the sample into the sample loops, a carrier flow tube, and a reciprocating multi-port valve to alternatively connect the sample loops to the carrier flow tube, so that a first sample is transferred through the carrier flow tube simultaneously to a second sample being drawn by the syringe into a second sample loop. Preferably, the sample loops comprise a length of no more than approximately ten centimeters. The sample loops preferably comprise an internal diameter of between approximately 0.005 to 0.01 inches, and also preferably comprise an internal volume of approximately no more than 5.0 $\mu$l, and more preferably approximately no more than 1.0 $\mu$l.

A preferred embodiment preferably comprises at least two syringes. The carrier flow tube preferably comprises a connection between said valve and a flow cytometer.

Preferably, the multi-port valve comprises a 2-position eight-port switching and sampling valve, and alternatively comprises a 6-port rotating valve comprising four engraved cavities, wherein the engraved cavities preferably comprise a volume of approximately 0.2 $\mu$l. Preferably, the multi-port valve comprises at least one inlet port, at least one outlet port, at least one transport stream inlet port, and at least one transport stream outlet port.

A preferred embodiment of the present invention also comprises a method for drawing and transporting multiple samples, the method comprising the steps of drawing a first sample into a sample loop with a syringe, changing a valve position, drawing at least one additional sample into an additional sample loop with a syringe, and expelling the sample from the sample loop with a carrier fluid. Preferably, the steps of drawing at least one additional sample and expelling the first sample are performed simultaneously. Preferably, a sample is drawn from a sample vessel. Preferably, the sample is drawn through at least one port in a reciprocating valve. Preferably, at least one additional sample is drawn from the same sample vessel, and alternatively from at least one additional sample vessel. Preferably, at least one valve is rotated to discontinue the flow from the sample vessel towards the syringe, and connect the sample loop with to a carrier flow tube. Additionally, the step of expelling the sample from the sample loop with a carrier fluid preferably comprises continuously pumping a buffer solution through a carrier flow tube.

An alternative embodiment of the present invention comprises a method for receiving and transporting multiple samples comprising the steps of pushing a first sample into a sample loop with a pump, changing a valve position, pushing at least one additional sample into an additional sample loop with a pump, and expelling the sample from the sample loop with a carrier fluid. Preferably the steps of pushing at least one additional sample and expelling the first sample are performed simultaneously. Preferably, the sample is pushed through at least one port in a reciprocating valve. Preferably, at least one valve is rotated to connect the sample loop to a carrier flow tube.

A primary object of the present invention is to provide a sample-processing apparatus with greatly reduced sample presentment time.

Another object of the present invention is to provide a flow cytometer sampling apparatus capable of quickly screening large libraries.

A further object of the present invention is to provide a flow cytometer sampling apparatus that obtains and processes more than one sample simultaneously.

A primary advantage of the present invention is the ability to draw and process more than one sample simultaneously.

A further advantage of the present invention is the elimination of the need of a separate rinsing/flushing step.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings.

DESCRIPTION OF THE PREFERRED EMBODIMENTS (BEST MODES FOR CARRYING OUT THE INVENTION)

The present invention is an apparatus for drawing and supplying multiple samples separated by buffer within a minute time frame. It allows for the rapid presentment and processing required in combinatorial library studies using flow cytometry. This much increased speed is effected by a series of sample loops, and at least one reciprocating valve. In combination, these allow for uptake and presentment of more than one unmixed sample at a time.

Figure 1:
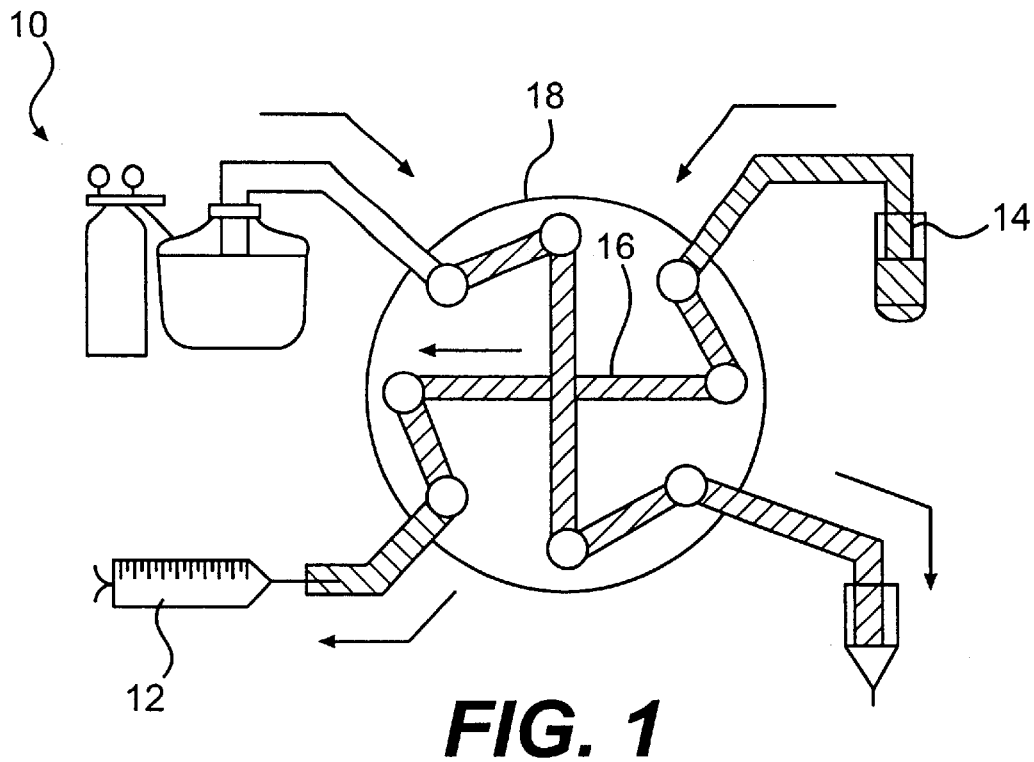
FIG. 1 is a top view of a preferred embodiment of the present invention, showing the valve in a first position, and showing first sample being drawn.
Figure 2:
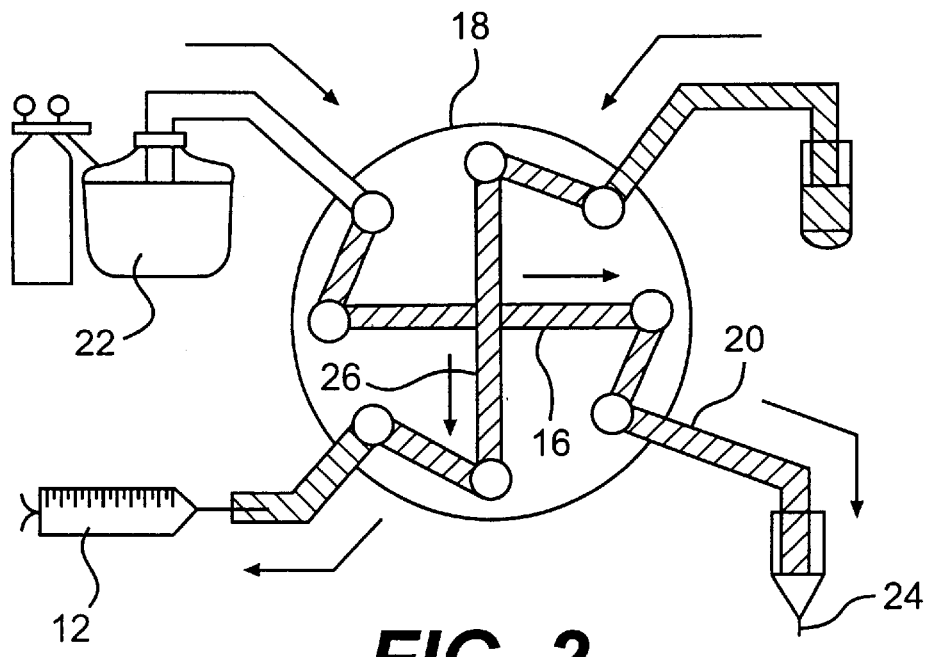
FIG. 2 is a top view of a preferred embodiment of the present invention, showing the valve in a second position.

A preferred embodiment 10 of the present invention is shown in FIGS. 1–2. As shown therein, syringe 12 draws sample 14 into first sample loop 16. When valve 18 switches positions, first sample loop 16 connects to fluid line 20, through which carrier buffer 22 is pumped. The sample is then pumped to flow cytometer 24 with the buffer. As the first sample flows to the point of analysis, syringe 12 draws a second sample aliquot into second sample loop 26. After valve 18 switches positions again, the second sample is pushed to flow cytometer 24 concomitant with drawing a third sample into first sample loop (not shown). Software controls the frequency at which this alternating cycle is repeated.

One problem encountered in most, if not all flow sample devices, is cross-contamination between sample plugs. This contamination is the result of either overlaps of sample peaks with the tails of preceding sample plugs, or particles from the preceding sample plug trapped in the valve junctions that join sample loops to the sampling and fluid flow lines. Under certain conditions, sample cross-contamination was determined to be 2–4%.

If reduction of sample cross-contamination to lower levels is absolutely necessary, however, this is accomplished in the present invention by increasing the sampling interval and/or reciprocating the sampling valve multiple times for each sample to completely clear the valve junctions. Such approaches decrease the maximal sample acquisition rate. Other approaches avoid the need to modify the sampling rate. One such approach is to fluorescently encode the particles in alternating adjacent sample wells with two distinctive fluorescent tags so that each successive sample has a tag distinct from that of the preceding sample. Such tags may include fluorochromes with distinctive fluorescence spectra or a single fluorochrome with distinctively different levels of fluorescence intensity. By establishing fluorescence analysis gates that exclude particles with the inappropriate tag, it is possible to eliminate contaminating particles from the analysis of each sample.

Figure 3:
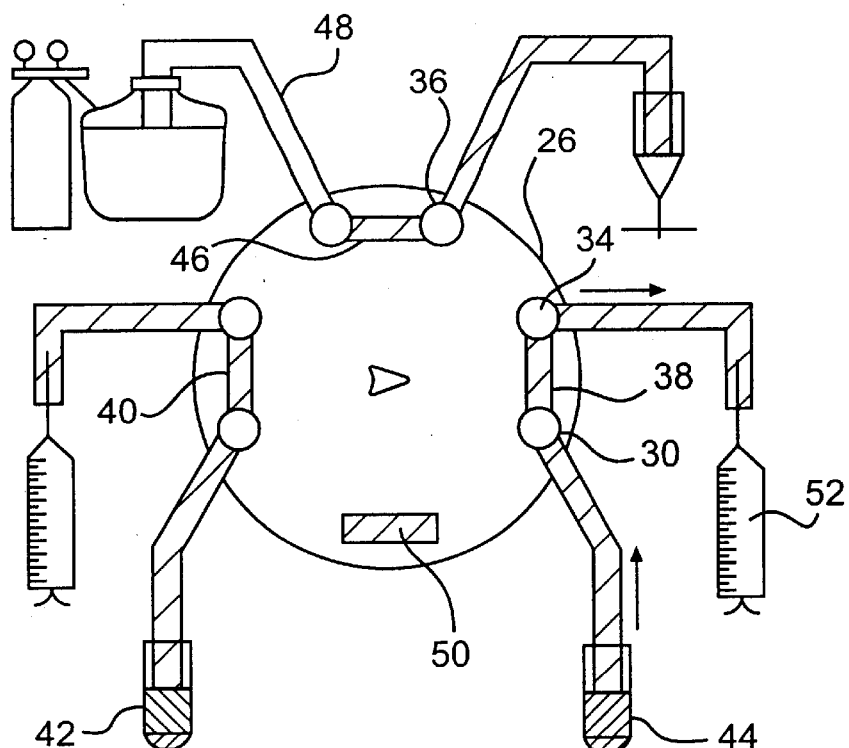
FIG. 3 is a top view of an alternative embodiment of the present invention showing sampling form two sample vessels and with valve in a first position.
Figure 4:
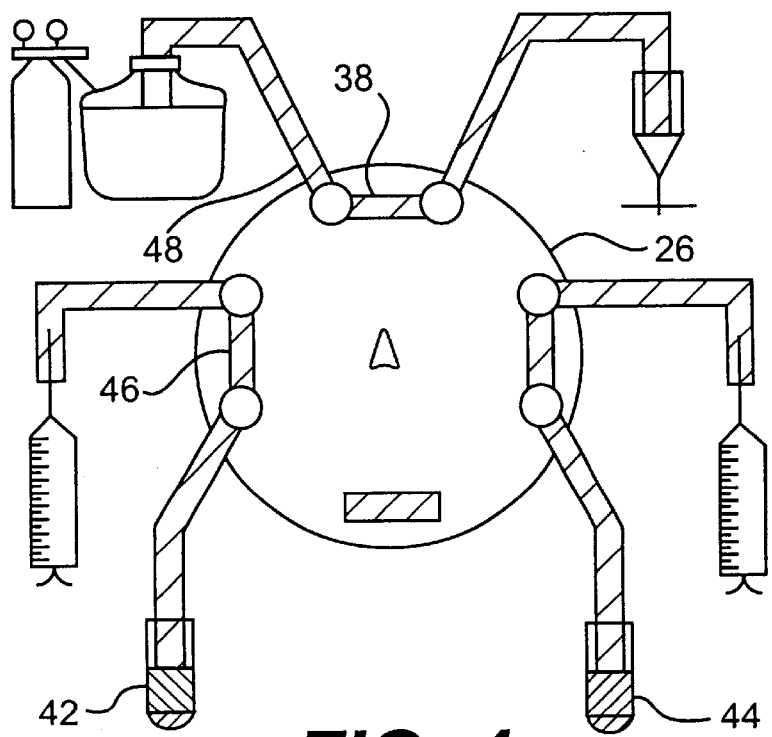
FIG. 4 is a top view of an alternative embodiment of the present invention showing sampling form two sample vessels and with valve in a second position.
Figure 5:
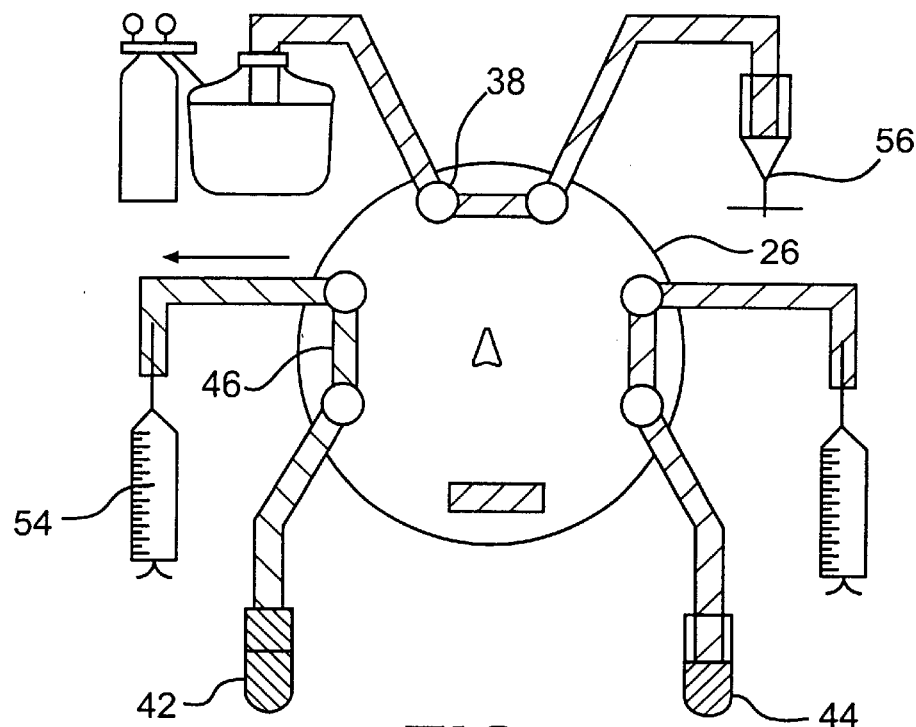
FIG. 5 is a top view of an alternative embodiment of the present invention showing sampling form two sample vessels and with valve in a second position, and showing second sample being drawn.
Figure 6:
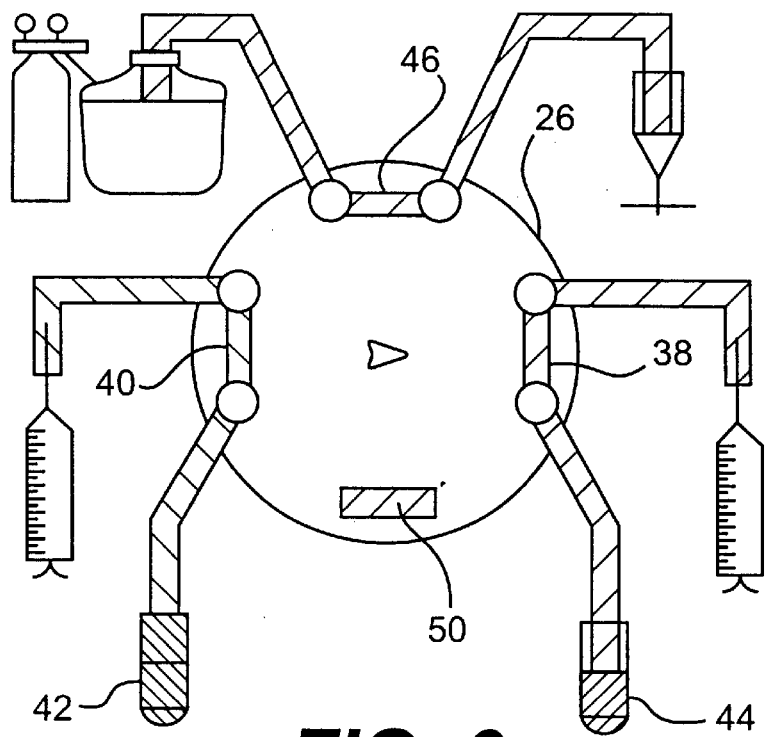
FIG. 6 is a top view of an alternative embodiment of the present invention showing sampling from two sample vessels and with valve returned to a first position after drawing the second sample.

An alternative embodiment of the present invention addresses the issue of sample plug cross-contamination, using an additional multi-port valve to connect the sample acquisition port to each of several separate sample ports. As shown in FIGS. 3–6, internal valve 26 containing cavities engraved thereon is alternatively positioned to connect to inlet ports 30, leading from sample vessels, outlet ports 34 and transport stream ports 36. In use, as shown in FIG. 3, initially cavities 38 and 40 are in-line with the flow paths from first and second sample vessels 42, 44, cavity 46 is connected to transport stream line 48, and cavity 50 is not in use. Second syringe pump 52 draws sample from second sample vessel 44 into cavity 38. Valve 26 switches positions, rotating the cavities counterclockwise to the second position, as shown in FIG. 4. There, cavity 38 is aligned with transport stream line 48, and cavity 46 is aligned with first sample vessel 42. As shown in FIG. 5, first syringe pump 54 draws sample from first sample vessel 42 into cavity 46 while the transport stream carries the sample plug from cavity 38 into flow cytometer 56. Valve 26 is then rotated clockwise to its original position, shown in FIG. 6, placing cavity 46 in line with transport stream line 48 so that the plug from cavity 46 is carried to flow cytometer 56. The process is then repeated.

Industrial Applicability

The invention is further illustrated by the following non-limiting examples.

An optimum sample-handling device is one that limits flow throughput only by sample preparation time and library handling procedure. Use of a 0.1 µl sample and 0.1 µl buffer plug at a sampling rate of 0.2 µl/sec (60 samples/min and 86,400 samples/day) allows detection and analysis of approximately 300 particles per sample, which is well within normal instrument capabilities. To reach this high productivity level, the preferred embodiment of the present invention utilizes interchangeable syringe barrels, at least one reciprocating valve, and a pressure-driven fluid line.

EXAMPLE 1

In one experiment, samples were aspirated with a Cavro XL3000 modular digital pump equipped with a 500 µl syringe barrel (Cavro Scientific Instruments, Sunnyvale, Calif.) and coupled to a VICI C22Z two-position eight-port switching and sampling valve with micro-electric actuator (Valco Instruments, Houston, Tex.). The syringe pump and valve were controlled by computer via a bi-directional RS232 port interface in which signals were routed with a four-port Mini Smart Switch (B&B Electronics, Ottawa, Ill.). Inserted into the valve were two sample loops, which consisted of 10 cm lengths of 0.01 inch internal diameter teflon tubing (to accommodate for the valve port connections) with an internal volume of approximately 5 µl (Upchurch Scientific). A 25×100 cm tube filled with distilled water or phosphate-buffered saline (GIBCO, Grand Island, N.Y.) was inserted into the sample port of a Coulter Elite flow cytometer as a reservoir of pressurized fluid. The fluid was continuously driven under pressure to the valve, through one of the sample loops, and on to the flow nozzle. Teflon tubing of 0.01 inch internal diameter was used to transport samples from the sample vessel to one of the valve sample loops, and to connect the loop to the aspirating syringe.

The total volume of sample to fill the aspiration tube and an adjoining loop of these dimensions was 10 $\mu$l. To routinely aspirate this, an additional 2 loop-volumes (20 $\mu$l) of sample was needed to completely displace any sample residue. Therefore, to obtain a 5 $\mu$l sample suitably pure for analysis, it was necessary to aspirate a total of 20 $\mu$l of sample.

The pressurized fluid was transported at a high fluid flow rate which generated a general broadening of light scatter and fluorescence intensity profiles that reflected suboptimal alignment of a proportion of the microspheres as they passed through the laser beam. Because good optical alignment is an important determinant of the sensitivity with which samples differing in fluorescence intensity can be discriminated, light scatter gating was used to focus the analysis exclusively upon the best aligned fraction of the sampled population. By determining the light scatter profile of optimally aligned microspheres under a low rate of continuous flow (0.8 $\mu$l/s) and constructing two light scatter gates based on this profile (one that tightly enclosed the aligned microsphere cluster (Gate 1) and another more relaxed gate (Gate 2) that enclosed a range of microsphere forward light scatter intensity approximately twice the size of Gate 2), the subfraction of rapidly flowing microspheres that remain properly aligned was selectively gated. When, under conditions of continuous flow, the flow rate was increased to 2.2 $\mu$l/s and 3.6 $\mu$l/s, there was a progressively increasing spread in the light scatter profile. There was also a corresponding broadening of the fluorescence intensity profiles of ungated microspheres when fluorescence data were acquired on either linear or log scales. By contrast, at both flow rates the fluorescence intensity profiles of microspheres falling within either of the two scatter gates exhibited only minor broadening relative to optimally aligned microspheres. Similar results were obtained under conditions of plug flow when the flow rates in the fluid line were established at 2.2 and 3.6 $\mu$l/s.

At a flow of 3.5 $\mu$l/s, a 5 $\mu$l plug took 7 seconds to traverse through the point of analysis (expected was 1.4 seconds). Therefore, the plug expanded in apparent length by five-fold (7/1.4) over a 14 cm path. When the path was shortened to 13 cm, the transit time equaled 5 seconds (3.6-fold expansion of plug length). From this, it was determined that a sample undergoes a 10–12% increase in length per cm traveled. Thus, the closer the loop to the point of analysis, the more samples analyzed/time without sample overlap due to plug expansion.

In 10 cm length tubing, expansion $\leq$3.1 fold so a 1.3 $\mu$l sample plug traveling at 3.5 $\mu$l/s is processed in approximately 1.2 seconds. A tubing of 0.005" internal diameter, of a length of 10 cm creates an internal volume of 1.3 $\mu$l (a four-fold reduction). Thus, only 1.3 $\mu$l of sample is required, reducing the aspiration time to less than 1 second. Therefore, to reach a goal of approximately 30 samples/minute, the following sequence is utilized:

(1) a sample is aspirated (1 second);
(2) a time delay is invoked (0.8 seconds); and
(3) the valve is switched (0.2 seconds). This sequence results in a time of 1.8 seconds between each valve switch, ample time to permit clearing of the sample loop.

EXAMPLE 2

Figure 7:
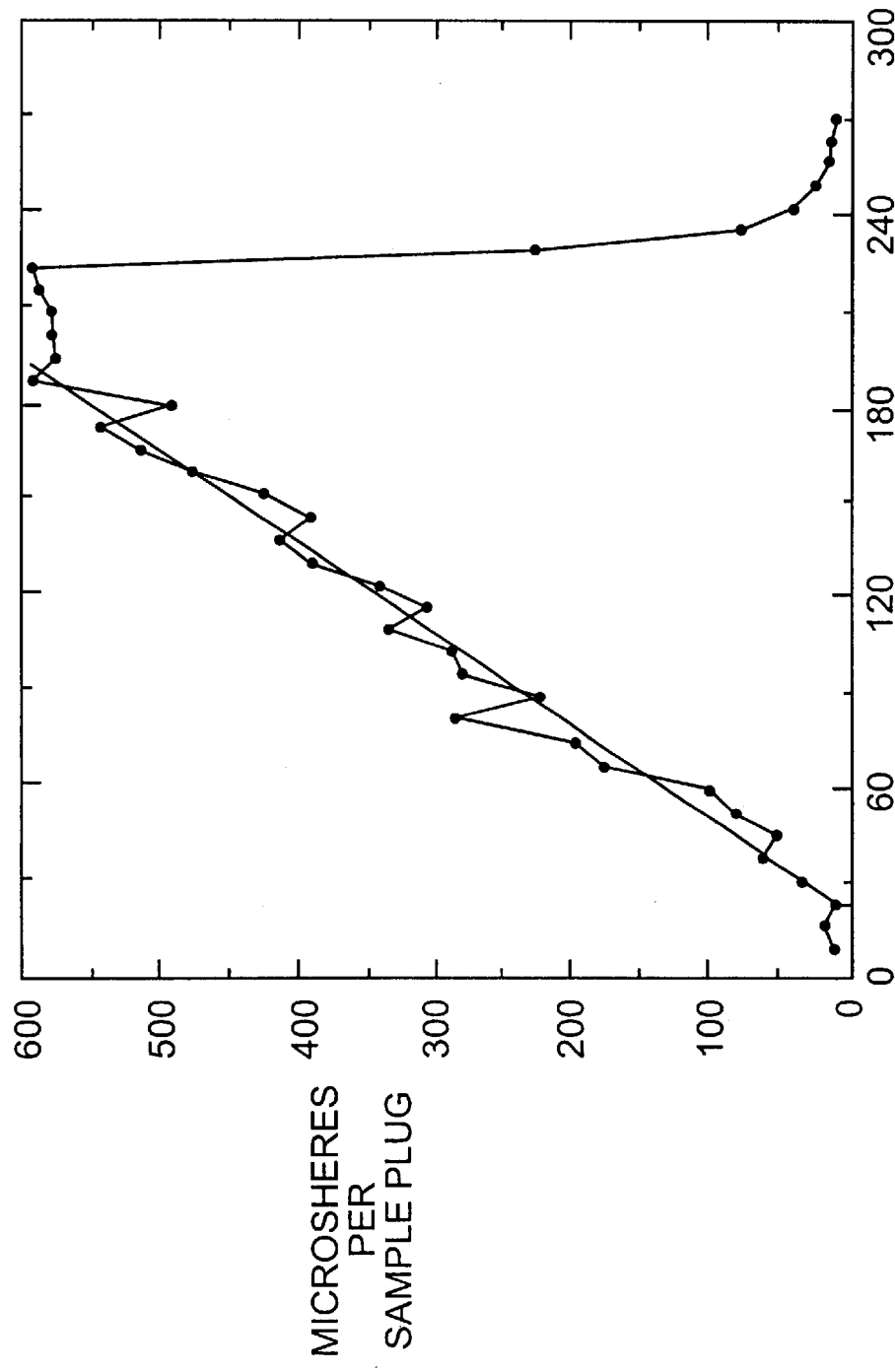
FIG. 7 is a graph of microsphere counts as a function of time using an alternative embodiment of the present invention comprising a pump.

In an alternative embodiment, the sample input port of the two-position eight port switching and sampling valve was attached to the output tube of a High Throughput Pharmacology System (HT-PS, Axiom Biotechnologies). The HT-PS was programmed to generate a gradient of fluorescent microspheres that ranged from 0 to 100% of the concentration of a stock input microsphere preparation. The microspheres were delivered from the HT-PS into the sample intake port of the plug flow coupling valve with a peristaltic pump. The coupling valve was reciprocated at 7 second intervals resulting in delivery of approximately 8.5 sample plugs per minute to the flow cytometer. The number of microspheres in each sample plug increased from 0 to 550 over a 150 second interval, in accordance with the HT-PS gradient programming. As shown in FIG. 7, a linear fit of microsphere counts as a function of time from 22 serially generated sample plugs resulted in a correlation coefficient R=0.986 and an estimated slope of 3.55±0.13 microspheres per second (an increase of approximately 25 microspheres per sample plug).

EXAMPLE 3

In an alternative embodiment for multiple sample vessels, a Valco C16Z 6-port internal sample injector valve with 4–0.2 $\mu$l internal cavities is used. Sample tubing has an internal diameter of 0.005 inches, and is 8 cm long. This determines an internal volume of 1.0 $\mu$l. Therefore, the total amount aspirated per sample drawn is 1.6 $\mu$l, equal to the sample tube volume plus three times the sample cavity volume. An aspiration time of 0.3 seconds, a flush time of 0.2 seconds, and a transit time of 0.2 seconds are easily accommodated by a valve cycle of 0.5 seconds. This allows for a 0.3-second gap between the tail of one plug and the next plug, and a sampling rate of two sample plugs per second.

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. An apparatus for transferring a plurality of samples, said apparatus comprising:
   a plurality of sample loops for receiving a plurality of samples;
   at least one device for moving said plurality of samples into said sample loops;
   a reciprocating multi-port valve to alternatively connect said sample loops to a carrier flow tube; and
   a flow cytometer connected to said multi-port valve by said carrier flow tube.

2. The Apparatus of claim 1, wherein said Sample loops comprises a length of no more than approximately ten centimeters.

3. The apparatus of claim 1, wherein said sample loops comprise an internal diameter of between approximately 0.005 to 0.01 inches.

4. The apparatus of claim 1, wherein said sample loops comprise an internal volume of approximately no more than 5.0 µl.

5. The apparatus of claim 4, wherein each of said sample loops comprises an internal volume of approximately no more than approximately 1.0 µl.

6. The apparatus of claim 1, wherein said apparatus comprises at least two syringes.

7. An apparatus for transferring a plurality of samples, said apparatus comprising:

a plurality of sample loops for receiving a plurality of samples;

at least one device for moving said plurality of samples into said sample loops; and a reciprocating multi-port valve to alternatively connect said sample loops to a carrier flow tube, wherein said multi-port valve comprises a 2-position eight-port switching and sampling valve.

8. An apparatus for transferring a plurality of samples, said apparatus comprising:

a plurality of sample loops for receiving a plurality of samples;

at least one device for moving said plurality of samples into said sample loops; and a reciprocating multi-port valve to alternatively connect said sample loops to a carrier flow tube, wherein said multi-port valve comprises a 6-port rotating valve comprising four engraved cavities.

9. The apparatus of claim 8, wherein said engraved cavities comprise a volume of approximately 0.2 µl.

10. The apparatus of claim 8, wherein said multi-port valve comprises at least one inlet port, at least one outlet port, at least one transport stream inlet port, and at least one transport stream outlet port.

11. The apparatus of claim 7, wherein said apparatus further comprises a flow cytometer connected to said multi-port valve by said carrier flow tube.

12. The apparatus of claim 8, wherein said apparatus further comprises a flow cytometer connected to said multi-port valve by said carrier flow tube.

* * * * *